(12) United States Patent
Tankovich

(10) Patent No.: US 10,675,481 B1
(45) Date of Patent: Jun. 9, 2020

(54) LASER SYSTEM FOR MULTIPLE BEAM TISSUE THERAPY

(71) Applicant: Nikolai Tankovich, San Diego, CA (US)

(72) Inventor: Nikolai Tankovich, San Diego, CA (US)

(*) Notice: Subject to any disclaimer, the term of this patent is extended or adjusted under 35 U.S.C. 154(b) by 0 days.

(21) Appl. No.: 16/546,267

(22) Filed: Aug. 20, 2019

(51) Int. Cl.
*A61N 5/06* (2006.01)
*A61N 5/02* (2006.01)
*A61N 7/00* (2006.01)
*A61N 5/067* (2006.01)

(52) U.S. Cl.
CPC .......... *A61N 5/0616* (2013.01); *A61N 5/022* (2013.01); *A61N 5/062* (2013.01); *A61N 7/00* (2013.01); *A61N 2005/067* (2013.01); *A61N 2005/0651* (2013.01); *A61N 2005/0654* (2013.01); *A61N 2005/0656* (2013.01); *A61N 2005/0658* (2013.01); *A61N 2007/0034* (2013.01)

(58) Field of Classification Search
None
See application file for complete search history.

(56) References Cited

U.S. PATENT DOCUMENTS

| | | | |
|---|---|---|---|
| 6,406,474 B1 | 6/2002 | Neuberger | |
| 8,251,982 B2* | 8/2012 | Zaghetto | A61N 5/0616 606/2 |
| 2006/0084953 A1* | 4/2006 | Tankovich | A61B 18/203 606/9 |

* cited by examiner

*Primary Examiner* — Brian T Gedeon
(74) *Attorney, Agent, or Firm* — TMB Law

(57) ABSTRACT

The invention provides a laser system and method for administering multiple beams of laser energy in tissue treatment applications. The system administers the beams simultaneously in a distribution pattern of spatially separated overlapping and non-overlapping regions on a tissue. The simultaneous administration and distribution pattern permit the beams to propagate within a tissue without producing the light scattering effects that characterize the sequential application of multiple laser beams to a tissue.

28 Claims, 5 Drawing Sheets the invention can avoid interference of the wavelengths by delivering the wavelengths simultaneously and in spatially separated and overlapping regions of the tissue being treated. By delivering the wavelengths simultaneously, the effects of multiple wavelengths of laser energy are produced in the tissue instantaneously thereby eliminating the need for a separate application of a subsequent wavelength which would necessarily be compromised by the earlier application of the preceding treatment wavelength. In addition, the laser system of the invention can spatially separate the wavelength beams on the treated tissue such that two wavelengths of laser energy are not applied to the same region of tissue thereby preventing a treated tissue from interfering with the propagation of a second wavelength of laser treatment. Spatial separation of multiple wavelengths of laser energy also permits the laser energy to penetrate tissues in different regions and at different depths thereby stimulating the tissues to release different therapeutic cytokines in different locations within the same tissue.

LASER SYSTEM FOR MULTIPLE BEAM TISSUE THERAPY

FIELD OF THE INVENTION

The invention relates to therapeutic electromagnetic radiation systems, and in particular, laser systems for use in tissue therapy.

BACKGROUND OF THE INVENTION

There are no lasers or laser handpieces on the market today that can simultaneously deliver two or more wavelengths of laser energy in spacial, fractional form. There are fractional lasers that can deliver one wavelength of laser energy. However, laser treatment usually requires different modalities of energy in order successfully treat the pathologies to which they are applied, such as skin pathologies. For example, the treatment of dermal rhytides from solar elastosis requires both deep and superficial laser effects on the skin to induce the skin to release therapeutic cytokines from the skin compartments, including the reticular dermis and papillary dermis. However, the sequential application of multiple wavelengths of laser energy compromises the treatment. The irradiation of the skin with a first wavelength of laser energy modifies the skin by coagulating tissue within the skin and causing it to swell. These effects alter the propagation of laser light within the skin such that the coagulated and swollen skin will swallow and scatter a second wavelength of laser energy that is subsequently applied in an effort to treat the skin. Moreover, the treated, swollen skin layer is inhibited in its ability to absorb therapeutic cytokines that are released by laser damage. The deficiencies of the sequential application of multiple laser wavelengths are even greater if one of the wavelength's energy beam is absorbed by water in the tissue, as is the case with laser wavelengths of 3, 5 and 10 micrometers.

Another example of the problems associated with the sequential application of different wavelengths of laser energy is provided by laser therapy of skin telangiectasias. Contemporary laser treatments for skin telangiectasias involve the application of a first laser system that emits a laser wavelength ranging between 528 nm to 595 nm to coagulate red blood vessels (i.e. small size telangiectasia), and the subsequent application of a second laser system that emits a laser wavelength ranging between 810 nm and 1080 nm to coagulate blue blood vessels (i.e. large size telangiectasia). Thus, current laser treatments for skin telangiectasias require the use of separate laser therapy systems having different wavelengths to coagulate both red and blue blood vessels in the skin, making the treatments inefficient, complicated, and costly.

What is needed in the art therefore is an effective laser therapy system that can simultaneously deliver multiple wavelengths of laser energy through the use of a single laser unit without producing interference between the wavelengths within the treated tissue.

SUMMARY OF THE INVENTION

The invention provides a therapeutic laser system that simultaneously delivers multiple wavelengths of laser energy using a single unit in a single application. The laser system delivers multiple wavelengths of laser energy without producing interference between the wavelengths that typically results when a tissue is treated with multiple wavelengths of laser energy in separate applications. The

REFERENCE NUMBERS

Figure 1:
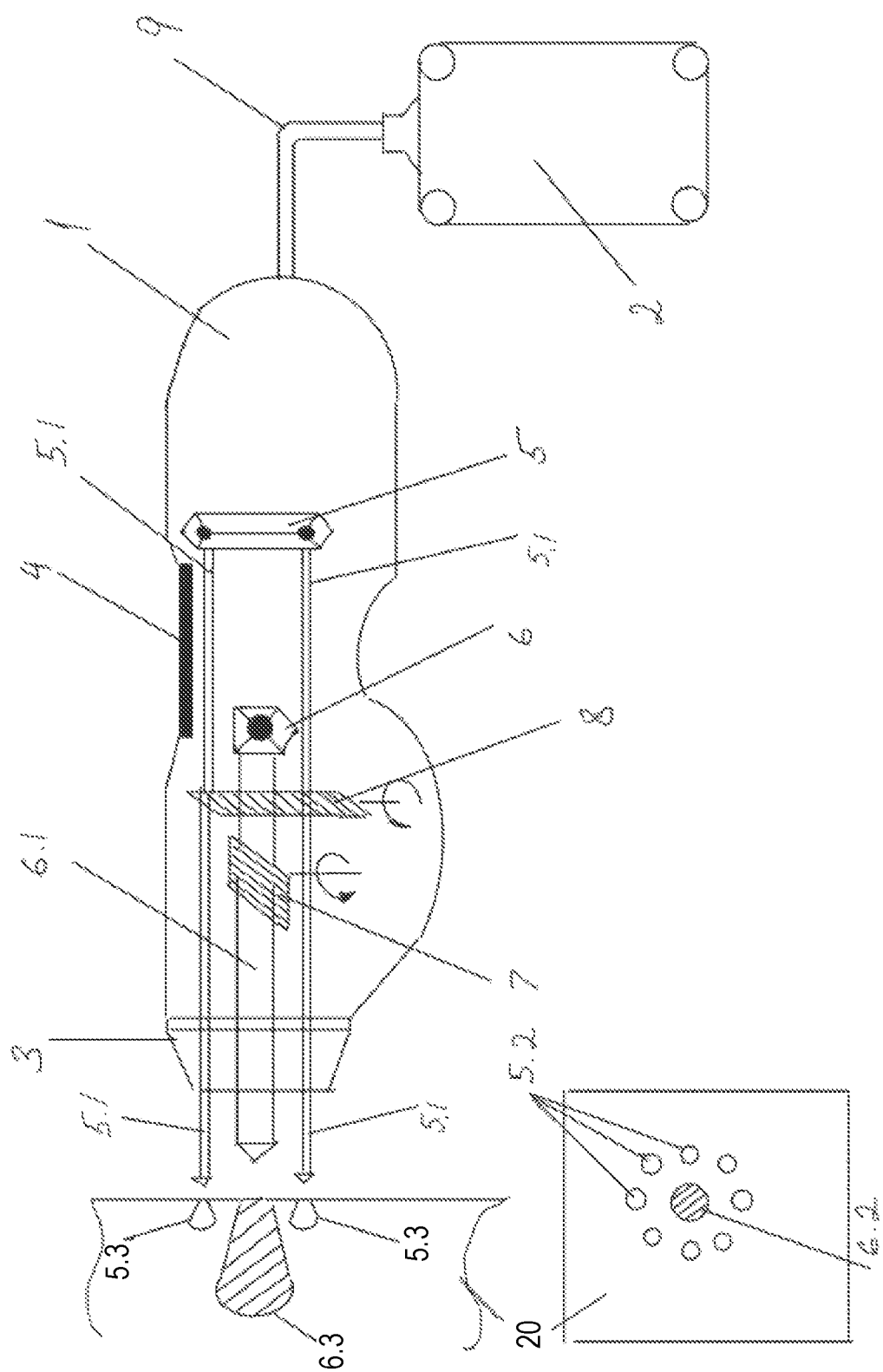
FIG. 1 shows an embodiment of the laser system of the invention.

1—Laser system
2—Power supply
3—Tip
4—Display
5—Laser
5.1—Beam from laser 5
5.2—Beam distribution pattern of beam 5.1
5.3—Propagation profile of beam 5.1
6—Laser
6.1—Beam of laser 6
6.2—Beam distribution pattern of beam 6.1
6.3—Beam propagation profile of beam 6.1
7—Fractional scanner for laser 6

8—Fractional scanner for laser 5
9—Power cord
10—Microwaves
11—Microwave generator
12—Microwave conductor
13—Intense pulsed light source
14—Fiber optic conductor
15—Non-coherent light
16—Ultrasound transducer
17—Ultrasound waves
18—Ultrasound transducer power supply
19—Power cord
CK1—Cytokines released laser 6.1
CK2—Cytokines released by laser 5.1
CK3—Cytokines released by the overlap of beams 5.1 and 6.1

Definitions

As used herein, the term "about" means the quantity, level, value, number, frequency, percentage, dimension, size, amount, weight or length that is referenced, or that varies (plus or minus) by as much as 30%, 25%, 20%, 15%, 10%, 9%, 8%, 7%, 6%, 5%, 4%, 3%, 2% or 1% of the referenced quantity, level, value, number, frequency, percentage, dimension, size, amount, weight or length.

As used herein, the phrase "skin condition" refers to a condition or disorder affecting the skin, including, without limitation, wrinkles, loss of skin elasticity, skin photoaging, scars, rhytides, acne, telangiectasia, vitiligo, skin lesions, tattoo removal, blepharoptosis, and combinations thereof.

As used herein, the phrase "skin lesion" refers to benign growths and lesions (e.g. actinic keratosis), neoplastic lesions (e.g. melanoma, basal cell carcinoma, and squamous cell carcinoma), skin wounds (e.g. burns, surgical wounds, cuts, and abrasions), diabetic ulcers, and bed sores.

As used herein, the terms "treat," "treating," and "treatment" can refer to the clinical intervention of a disease or condition in an attempt to alter, alleviate, ameliorate, prevent, lessen or reverse the progression or symptoms of the disease or condition.

As used herein, the phrase "cytokine profile" refers to the cytokines, chemokines, and other biomolecules that are released from a tissue or collection of cells that results from contacting the tissue or collection of cells with laser energy. The contact can result in the tissue or collection of cells being ruptured, cauterized, heated, or otherwise damaged. Cytokine profiles can be released from skin one or more skin structures, such as the epidermis, papillary dermis, and dermis.

DETAILED DESCRIPTION

The invention relates to a laser system and method for delivering multiple wavelengths of laser energy in the treatment of tissue conditions, such as conditions of the skin. The laser system delivers multiple wavelengths of laser energy without the wavelengths interfering with one another in the tissues to which they are applied. The laser system can avoid interference of the wavelengths by simultaneously delivering overlapping and non-overlapping wavelengths in spatially separated areas of application.

FIG. 1 depicts an embodiment of the laser system of the invention. In this embodiment, laser system 1 is in electrical communication with power supply 2 through power cord 9. Laser system 1 has laser 5 that generates beam 5.1, and laser 6 which generates beam 6.1. Laser 5 and laser 6 can be solid-state lasers, laser diode lasers (e.g. diode pumped fiber lasers and diode pumped Tm-doped fiber lasers), gas lasers, chemical lasers, dye lasers, metal-vapor lasers, semiconductor lasers, or combinations thereof. For example, laser 5 can be a laser diode, and laser 6 can be a solid-state laser. Alternatively, laser 5 and laser 6 can be the same type of laser. For example, laser 5 and laser 6 can be a pair of gas lasers, a pair of laser diodes, or a pair of solid state lasers. In some aspects of the invention, laser 5 and laser 6 are dermatological lasers, ophthalmic lasers, surgical lasers, or cosmetic lasers. Laser 5 and laser 6 can be a combination of lasers comprising a diode pumped Tm-doped fiber laser and a solid state Er:YSGG laser. In some aspects of the invention, laser 5 and laser 6 are laser diodes or diode pumped fiber lasers. The laser diodes can individually have a power of one thousandth of a Watt, one hundredth of a Watt, one tenth of a Watt, half a Watt, one Watt, one dozen Watts, two dozen Watts, three dozen Watts, four dozen Watts, five dozen Watts, six dozen Watts, seven dozen Watts, or more. Laser 5 and laser 6 can generate lasers in pulse beam mode, continuous beam mode, or a combination thereof. For example, laser 5 can generate beam 5.1 in pulse mode, while laser 6 generates beam 6.1 in continuous mode. The pulse beam mode can produce a pulse having a duration from about a dozen femtoseconds to about one or more seconds. In some aspects of the invention, laser system 1 is a laser handpiece.

In at least one aspect of the invention, beam 5.1 and beam 6.1 have different wavelengths. Beam 5.1 and beam 6.1 can have different wavelengths selected from about 540 nm, about 700 nm, about 810 nm, about 980 nm, about 1064 nm, about 1300 nm, about 1440 nm, about 1450 nm, about 1550 nm, about 1927 nm, about 1940 nm, about 2790 nm, about 2790 nm, about 2940 nm, and about 10600 nm. Non-limiting pairings for the wavelengths of beam 5.1 and beam 6.1, include, but are not limited to about 1550 nm and about 1930 nm, about 980 nm and about 1550 nm, about 980 nm and about 1930 nm, about 810 nm and about 1030 nm, about 1440 nm and about 1930 nm, about 532 nm and about 540 nm, about 532 nm and about 980 nm, about 1927 nm and about 1440 nm, about 577 nm and about 980 nm, and about 540 nm and about 980 nm. In at least one aspect of the invention, beam 5.1 and beam 6.1 can have the same wavelength, including without limitation the wavelengths disclosed herein. The wavelengths for the beams can be selected based on their ability to propagate within a tissue or group of cells that is desired to be illuminated with laser energy, it being understood that chromatophores selectively absorb certain wavelengths of laser energy.

Laser system 1 includes fractional scanner 7 which is in optical communication with laser 6 to distribute beam 6.1, and fractional scanner 8 which is in optical communication with laser 5 to distribute beam 5.1. In some aspects of the invention, fractional scanners 7 and 8 are optical laser mirrors in mechanical communication with scanner motors (not shown) that are adapted to move the mirrors in a manner that reflects the mirrors' respective beams to produce a desired distribution pattern of laser light. The motors are adapted to receive instructions from a processor (not shown) within laser system 1 for executing a pattern of movement that moves scanners 7 and 8 in a manner that reflects and distributes beams 5.1 and 6.1 in a desired distribution pattern of laser light. For example, fractional scanner 7 can be moved by its motor according to a first pattern that reflects beam 6.1 to achieve beam distribution pattern 6.2, while fractional scanner 8 can be moved by its motor according to a second pattern that reflects beam 5.1 to achieve beam distribution pattern beam 5.2. Fractional scanners 7 and 8 can control the number of distribution spots for the beams, wherein greater motor speeds provide a greater number distribution spots, and slower motor speeds providing fewer distribution spots. Fractional scanner 7 and fractional scanner 8 can be moved by their respective motors to distribute beams 5.1 and 6.1 in a pattern selected from overlapping beams, partially overlapping beams, non-overlapping beams, and combinations thereof. In some aspects of the invention, the scanner motors are substituted with one or more solenoids, one or more magnetic coils, or a combination thereof.

In some aspects of the invention, scanners 7 and 8 are beam separation windows having a pair of opposing planar surfaces. The beam separation windows can be made of sapphire, thermoconductive glass, or other material suitable for transmitting laser light. The beam separation windows can be arranged within laser system 1 such that beams 5.1 and 6.1 contact the beam separation windows in an orientation that is perpendicular, or generally perpendicular, to the planar surfaces of the windows. Each beam separation window comprises a coating on at least one planar surface that blocks the transmission of laser energy. The coatings can be blocking for one or more wavelengths of laser energy. Suitable materials for the coating include, but are not necessarily limited to, evaporated metal films (e.g. aluminum and/or gold), silica, scandium oxide, magnesium fluoride, hafnium fluoride, or combinations thereof. The coatings have one or more openings that permit at least a portion of a laser beam to be transmitted through the beam separation windows to produce a desired beam distribution pattern. For example, the beam separation window of scanner 7 can have a plurality of openings in the coating to split beam 5.1 into a plurality of beams, while the beam separation window of scanner 8 comprises a single opening in its coating to constrict beam 6.1 to a beam having a smaller cross-section. In such configurations, it will be understood that lasers 5 and 6 generate their respective beams with a cross section that is sufficiently large to cover at least a portion of the openings in the coatings on the windows. The openings in the windows can be arranged to transmit beams 5.1 and 6.1 in a beam distribution pattern selected from overlapping beams, partially overlapping beams, non-overlapping beams, and combinations thereof. The openings in the coatings can be arranged to produce the various configurations for beam distribution pattern 5.2 and beam distribution pattern 6.2 as disclosed herein.

FIG. 1 depicts a non-limiting beam distribution pattern on skin 20 of a patient wherein fractional scanner 8 is adapted to distribute beam 5.1 according to beam distribution pattern 5.2, and fractional scanner 7 is adapted to distribute beam 6.1 according to beam distribution pattern 6.2, such that beams 5.1 contacts skin 20 in a pattern that surrounds the areas of skin 20 that are contacted by beam 6.1. In this pattern, beams 5.1 and 6.1 contact skin 20 in a spatially separated, non-overlapping areas. The side view of skin 20 shows beam propagation profile 5.3 indicating that beam 5.1 can propagate deeper within skin 20 than beam propagation profile 6.3 of beam 6.1. The side view of skin 20 further shows that the areas of skin 20 where the beams propagate are spatially separated and non-overlapping.

Figure 2:
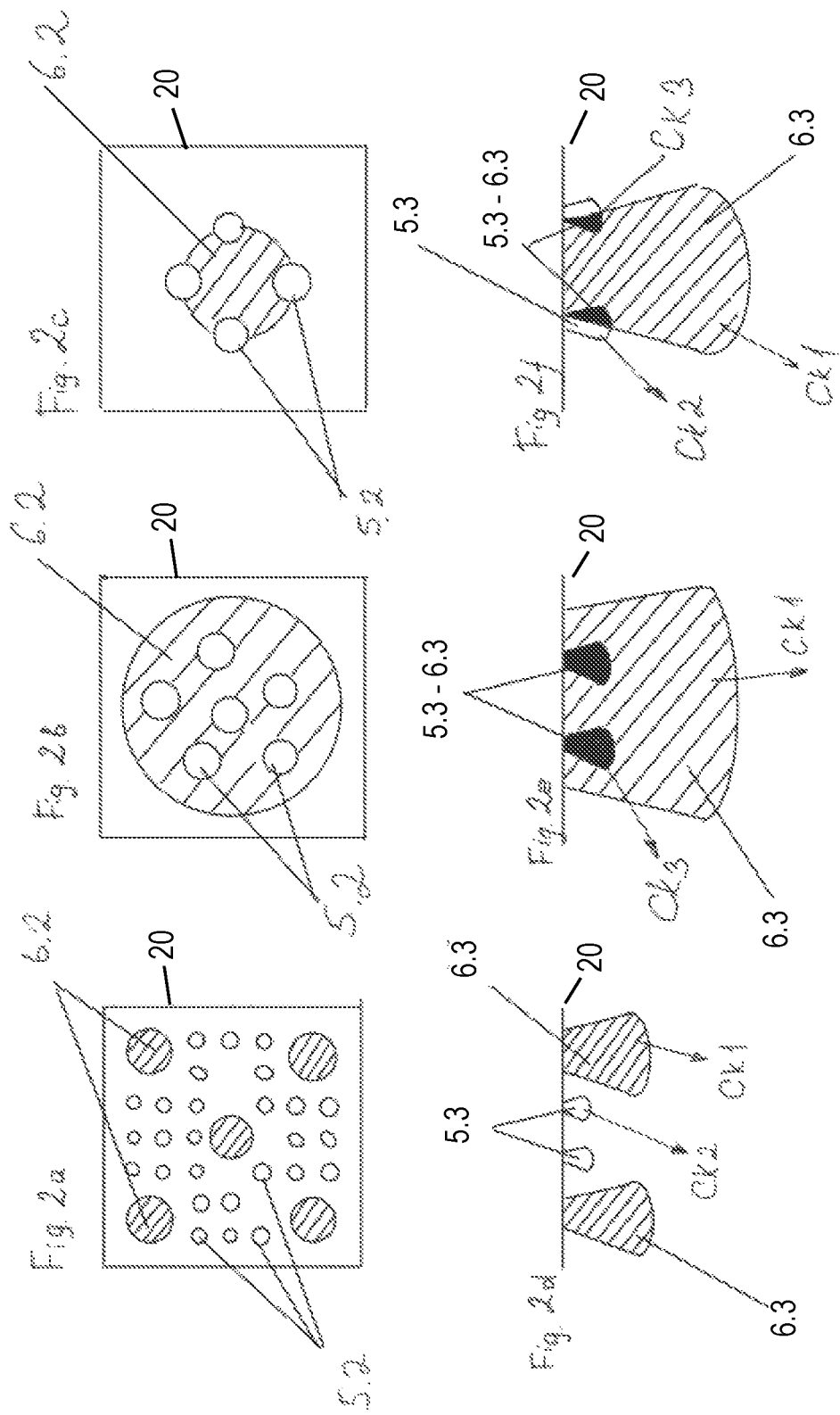
FIG. 2A shows a cross-section of a non-limiting, non-overlapping beam distribution pattern provided by the laser system of the invention.
FIG. 2B shows a cross-section of a non-limiting, fully overlapping beam distribution pattern provided by the laser system of the invention.
FIG. 2C shows a cross-section of a non-limiting, partially overlapping beam distribution pattern provided by the laser system of the invention.
FIG. 2D is a side view of the beam distribution of pattern of FIG. 2A showing the effects of the simultaneous application of non-overlapping wavelengths of laser energy in a tissue.
FIG. 2E is a side view of the beam distribution of pattern of FIG. 2B showing the effects of the simultaneous application of fully overlapping wavelengths of laser energy in a tissue.
FIG. 2F is a side view of the beam distribution of pattern of FIG. 2C showing the effects of the simultaneous application of partially overlapping wavelengths of laser energy in a tissue.

Fractional scanner 7 and fractional scanner 8 can be adapted to provide other beam distribution patterns, such as the non-limiting patterns depicted in FIGS. 2A, 2B, and 2C. FIG. 2A depicts a planar view of skin 20 wherein scanner 8 distributes beam 5.1 according to beam distribution pattern 5.2, and scanner 7 distributes beam 6.1 according to beam distribution pattern 6.2 such that beam 5.1 contacts skin 20 in spatially separated spots interspersed between the spots contacted by beam 6.1 without overlapping of the beams. FIG. 2D is a side view of skin 20 from FIG. 2A depicting the propagation of beams 5.1 and 6.1 in the skin, wherein beam propagation profile 5.3 shows beam 5.1 does not propagate as deeply as the beam propagation profile of beam 6.1, and that beam propagation profiles 5.3 and 6.3 do not overlap within skin 20. In some aspects of the invention, beam 5.1 can have a wavelength of about 1927 nm, wherein beam propagation profile 5.3 occupies only the epidermis at a depth of between about 30 microns and 50 microns, while beam 6.1 can have a wavelength of about 1550 nm, wherein beam propagation profile 6.3 occupies the papillary dermis at a depth of between about 150 microns and 200 microns.

FIG. 2D also depicts the release of cytokine profile CK2 from the area of skin 20 that is occupied by beam propagation profile 5.3, and the release of cytokines CK1 from the area of skin that is occupied by beam propagation profile 6.3. Without being limited to any particular theory or mechanism, contacting tissues, such as skin, with laser light can create zones of damage in the areas where the laser light propagates in the tissue, leading the damaged tissue to release cytokines which migrate from the zone of damage to produce a therapeutic effect in the surrounding, undamaged tissue. For example, contacting the skin with wavelength of laser energy that propagates within the epidermis can create a zone of damage in this tissue compartment leading to the release of a first cytokine profile, while contacting the skin with a second wavelength of laser energy that propagates in the papillary dermis can create a zone of damage in this tissue compartment leading to the release of a second cytokine profile.

FIG. 2B depicts a planar view of skin 20 wherein scanner 8 distributes beam 5.1 according to beam distribution pattern 5.2 and scanner 7 distributes beam 6.1 according to beam distribution pattern 6.2, such that beam 5.1 overlaps beam 6.1 on skin 20. FIG. 2E is a side view of skin 20 from FIG. 2B depicting the propagation of beams 5.1 and 6.1 in the skin, wherein propagation profile 6.3 shows that beam 6.1 propagates more deeply than beam 5.1 in the region of skin depicted by beam propagation profile 5.3-6.3 where beams 5.1 and 6.1 overlap. FIG. 2E shows the release of cytokines CK1 from the area of skin 20 that is occupied by beam propagation profile 6.3 and the release of cytokines CK3 from the area of skin 20 that is occupied by beam propagation profile of 5.3-6.3. In some aspects of the invention, the beam propagation profiles of FIG. 2E can be such that beam 5.1 is produced by an Er:YSGG solid-state laser at a wavelength of about 2790 nm, wherein beam propagation profile 5.3 occupies the epidermis at a depth between about 10 microns and about 30 microns, and beam 6.1 has a wavelength of about 1550 nm wherein beam propagation profile 6.3 occupies the papillary dermis at a depth between about 150 microns and about 200 microns. In such an aspect, it will be understood that cytokine profile CK1 will be produced by beam 6.1 damaging the papillary dermis, and cytokine profile CK3 will be produced by beams 5.1 and 6.1 damaging the epidermis.

FIG. 2C depicts a planar view of skin 20 wherein scanner 8 is adapted to distribute beam 5.1 according to beam distribution pattern 5.2 and scanner 7 is adapted to distribute beam 6.1 according to beam distribution pattern 6.2. In such a configuration, a portion of beam 5.1 overlaps beam 6.1. FIG. 2F is a side view of skin 20 from FIG. 2C depicting the propagation of beams 5.1 and 6.1 in the skin wherein beam propagation profile 6.3 shows beam 6.1 propagates more deeply than beam 5.1. Beam propagation profile 5.3-6.3 depicts a region of skin wherein overlapping beams 5.1 and 6.1 both propagate within skin 20. FIG. 2F shows the release of cytokine profile CK1 from beam propagation profile 6.3, the release of cytokine profile CK2 from beam propagation profile 5.3, and the release of cytokine profile CK3 from beam propagation profile 5.3-6.3. The beam propagation profiles depicted in FIG. 2F can be produced by laser system 1 having a configuration wherein laser 5 is laser diode that produces beam 5.1 at a wavelength of about 1440 nm, and laser 6 is a laser diode that produces beam 6.1 at a wavelength of between about 810 nm and about 980 nm. This configuration can produce beam propagation profile 5.3 and beam propagation profile 5.3-6.3 wherein beam 5.1 propagates within the papillary dermis at a depth of between about 120 microns and about 180 microns, and beam propagation profile 6.3 wherein beam 6.1 propagates within all dermal layers of the skin at a depth between about 4 mm and about 5 mm.

In some aspects of the invention, laser system 1 comprises tip 3. Tip 3 can be a disposable unit that detachably connects to laser system 1. Tip 3 can have one or more reservoirs adapted to contain cosmetics, therapeutic compositions, or combinations thereof. Tip 3 can be adapted to contain compositions including, but not necessarily limited to, drugs (e.g. Avastin™ and Lucentis™), anti-angiogenic antibodies, hyaluronic acid, Botox™, fibroblasts, stem cells, stem cell factors, vitamins, antioxidants, and combinations thereof.

In some aspects of the invention, the laser system includes a display for inputting operation parameters and displaying system feedback. FIG. 1 depicts laser system 1 with display 4 for communicating with a processor within laser system 1 (not shown). Display 4 is configured to display information relating to the operation of laser system 1, such as the power of beams 5.1 and 6.1, the wavelengths of beams 5.1 and 6.1, the pulse duration of the beams, and the number of laser pulses and the amount of laser energy delivered. Display 4 can be configured to receive input from a user, such input including turning laser system 1 on and off, selection of a desired power for each of beams 5.1 and 6.1, the laser mode for the lasers (e.g. pulse or continuous mode), and the duration of the beam pulses, for example.

Figure 3:
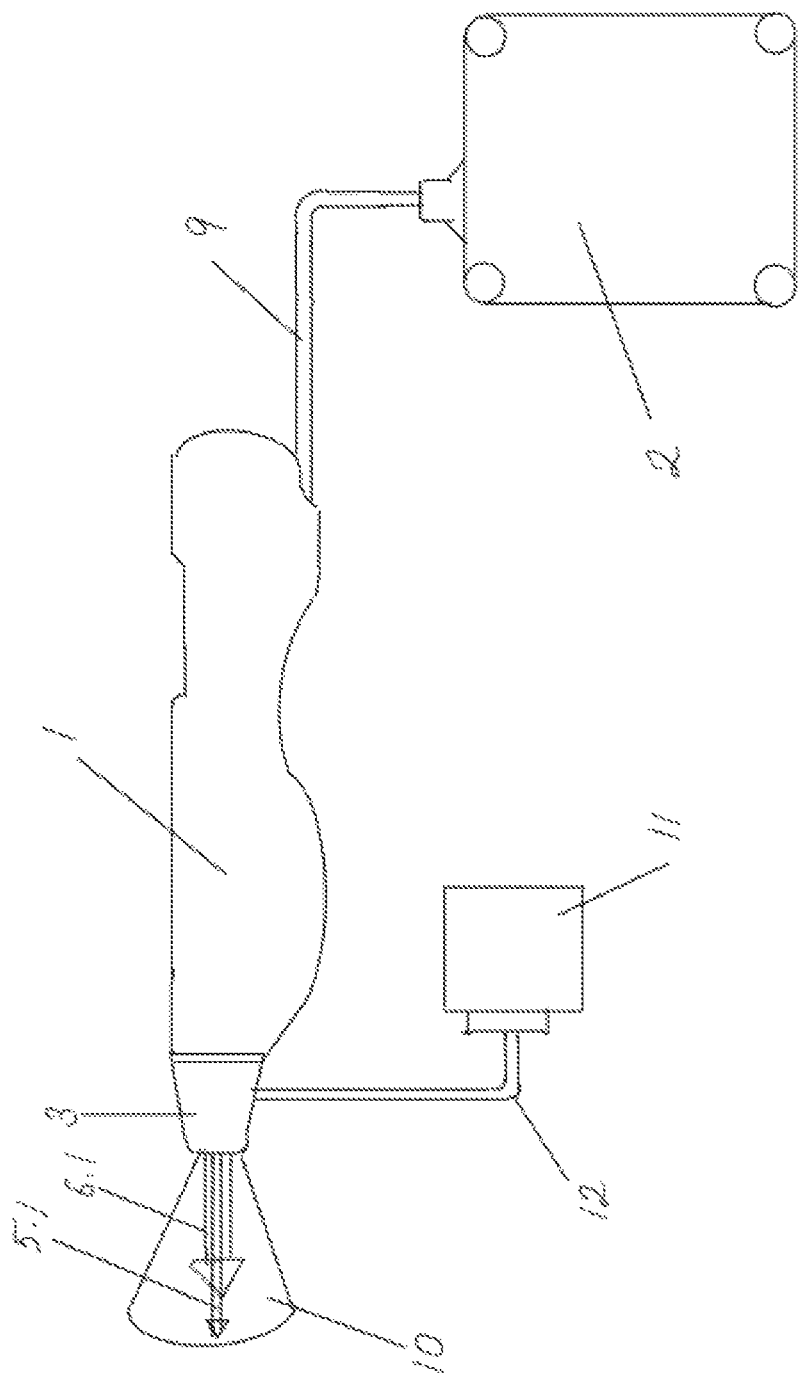
FIG. 3 shows an embodiment of the laser system of the invention having a tip adapted to emit microwave radiation.

FIG. 3 depicts a non-limiting embodiment of the invention wherein laser system 1 comprises tip 3 which is adapted to emit microwave energy. In this embodiment, tip 3 is in electronic communication with microwave generator 11 through microwave conductor 12 such that laser unit 1 is adapted to simultaneously administer microwaves 10, beam 5.1, and beam 6.1 onto a treated tissue, such as the skin of a patient, for example. It will be understood that in this embodiment, display 4 is adapted to monitor and control the operation of microwave generator 11. In some aspects, laser system 1 comprises an integrated microwave generator housed within the system rather than in the tip.

Figure 4:
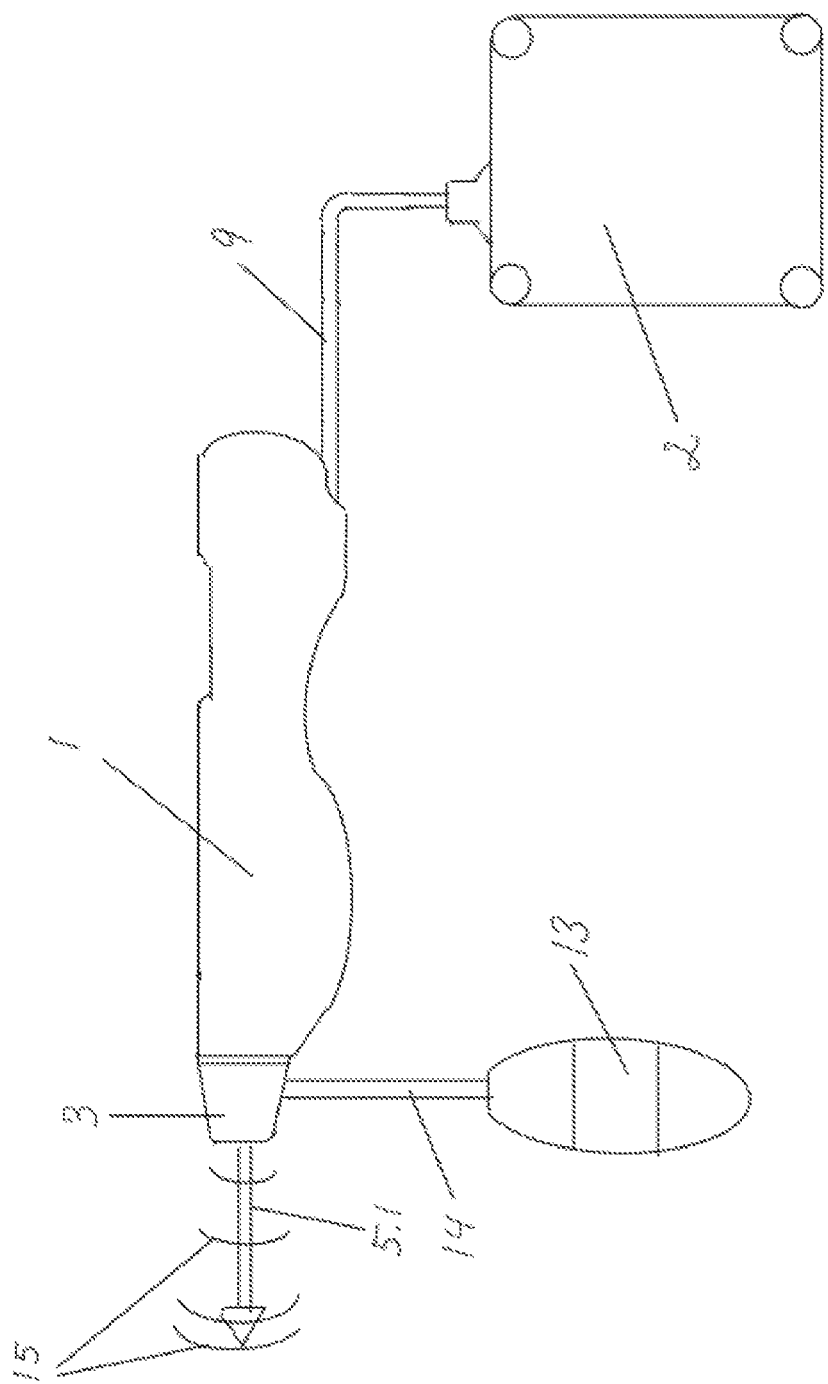
FIG. 4 shows an embodiment of the laser system of the invention having a tip adapted to emit non-coherent light.

FIG. 4 depicts a non-limiting embodiment of the invention wherein laser system 1 comprises tip 3 which is adapted to emit intense pulsed light. In this embodiment, tip 3 is in optical communication with intense pulsed light source 13 through fiber optic conductor 14 such that laser unit 1 is adapted to simultaneously administer non-coherent light 15, beam 5.1, and beam 6.1 onto a treated tissue, such as the skin of a patient, for example. It will be understood that in this embodiment display 4 is adapted to monitor and control the operation of intense pulsed light source 13. In some aspects, laser system 1 comprises an integrated intense pulsed light source housed within the system rather than in the tip.

Figure 5:
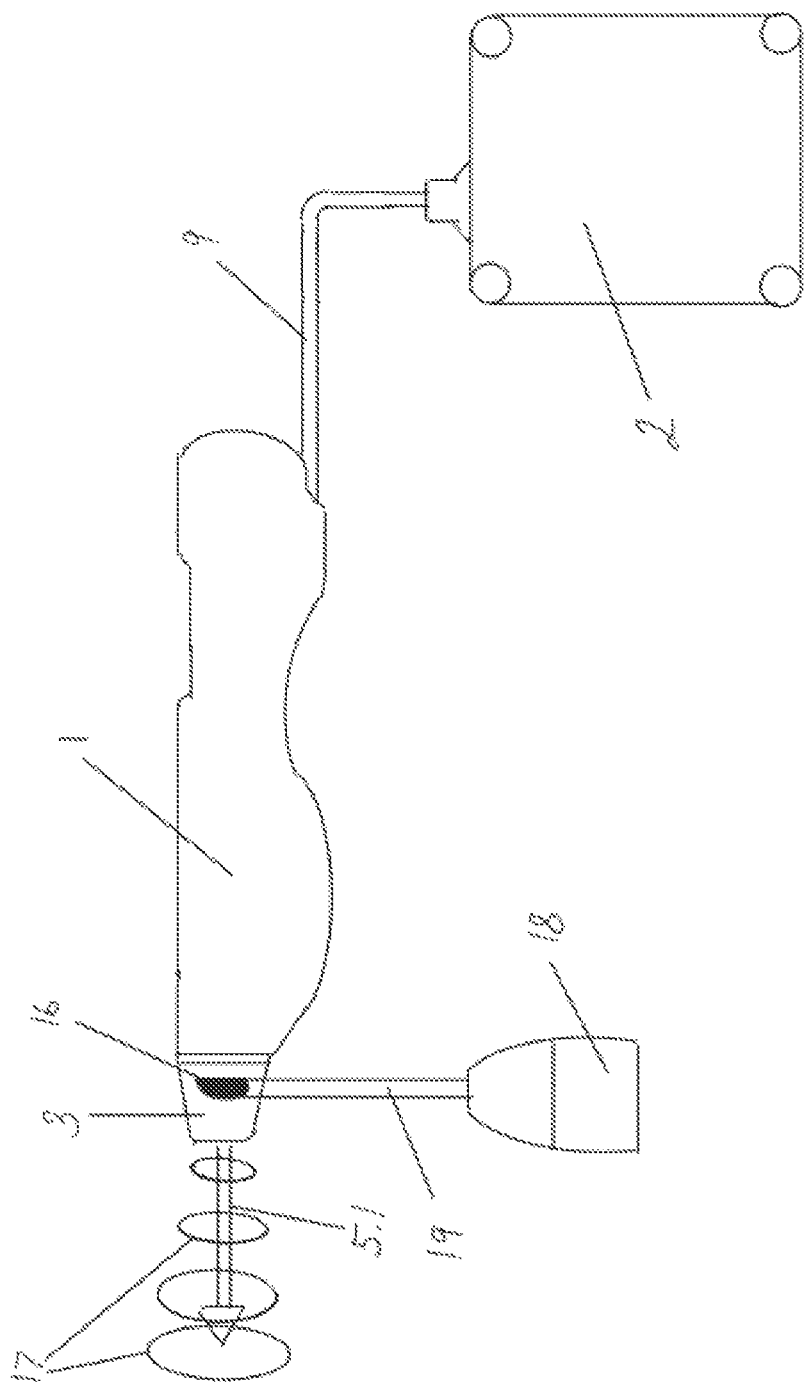
FIG. 5 shows an embodiment of the laser system of the invention having a tip adapted to emit ultrasonic energy.

FIG. 5 depicts a non-limiting embodiment of the invention wherein laser system 1 comprises tip 3 which is adapted to emit ultrasound. In this embodiment, tip 3 comprises ultrasound transducer 16 which is in electronic communication with ultrasound transducer power supply 18 through power cord 19. In this embodiment, laser unit 1 is adapted to simultaneously administer ultrasound waves 17, beam 5.1, and beam 6.1 (not shown) onto a treated tissue, such as the skin of a patient, for example. It will be understood that in this embodiment display 4 is adapted to monitor and control the operation of ultrasound transducer 16. In some aspects, laser system 1 comprises an integrated ultrasound transducer housed within the system rather than in the tip.

In some aspects, the invention provides a method of treating a tissue with two or more beams of laser energy. In one embodiment, the method is practiced by providing laser system 1 as disclosed herein, and contacting a tissue with beams 5.1 and 6.1 simultaneously according to the beam the distribution patterns disclosed herein. Beams 5.1 and 6.1 can have the same or different wavelengths and can have the same or different mode. The beam distribution patterns result in beams 5.1 and 6.1 contacting the tissue in a pattern selected from overlapping beams, partially overlapping beams, non-overlapping beams, and combinations thereof. Contacting the tissue with the beams causes the beams to propagate within the tissue in overlapping or spatially separated areas of the skin to produce zones of tissue damage leading the damaged tissues to release a cytokine profile into the surrounding, undamaged tissues. By contacting the tissue simultaneously and in spatially separated areas, beams 5.1 and 6.1 are prevented from interfering with one another since each beam contacts tissue that has not been damaged by laser light, it being understood that tissue that has been damaged by laser light can scatter and absorb a subsequent application of laser light and prevent the efficient propagation of the subsequent application of laser light within the tissue.

The method can comprise administering, simultaneously with the two or more beams of laser energy, at least one of ultrasound energy, microwave energy, and intense pulsed light. It is also contemplated that the method can comprise topically administering a composition during or after the application of laser energy. In some aspects, the composition is administered from within a reservoir in tip 3. The composition can be any composition that has a cosmetic or therapeutic effect on the skin condition being treated. Suitable compositions include, but are not limited to, drugs (e.g. Avastin™ and Lucentis™), anti-angiogenic antibodies, hyaluronic acid, Botox™ fibroblasts, stem cells, stem cell factors, vitamins, antioxidants, and combinations thereof.

In some aspects of the method, beams 5.1 and 6.1 propagate in the treated tissue in a pattern of overlapping beams, partially overlapping beams, non-overlapping beams, or combinations thereof. Beams 5.1 and 6.1 can also propagate at different depths. For example, beam 5.1 can propagate within the tissue at a depth that is shallower than the propagation of beam 6.1. For example, when laser system 1 is used to treat the skin, beam 5.1 can propagate only within the stratum corneum or epidermis, and beam 6.1 can propagate to a depth that reaches the papillary dermis or all dermal layers of the skin.

Beams 5.1 and 6.1 can have the same or different mode. The beams can be administered in a pulse beam mode, a continuous beam mode, or a combination thereof. The beams can have the same or different wavelengths, wherein the wavelengths are selected from about 540 nm, about 700 nm, about 810 nm, about 980 nm, about 1064 nm, about 1440 nm, about 1300 nm, about 1440 nm, about 1550 nm, about 1927 nm, about 1940 nm, about 2790 nm, about 2940 nm, about 10600 nm, about 1550 nm, and about 2790 nm.

In at least one aspect, the method can be used to treat a skin condition. The skin condition can be any skin condition capable of being treated with two or more beams of laser energy. The skin condition can be wrinkles, loss of elasticity, skin photoaging, scars, rhytides, acne, telangiectasia, vitiligo, skin lesions, tattoo removal, blepharoptosis, or combinations thereof.

In one non-limiting embodiment, the invention provides a method of treating skin aging, wherein laser 5 comprises a laser diode that produces beam 5.1 in pulse mode at wavelength of about 1930 nm, and laser 6 produces beam 6.1 at a wavelength of about 1550 nm. A composition comprising at least one of vitamins, antioxidants, and stem cell factors is administered to the skin of the patient with or after the application of the laser energy. Without being limited to any particular theory or mechanism, the application of the laser energy perforates the skin permitting the composition to permeate the skin more efficiently. For example, the application of beam 5.1 can perforate the stratum corneum which would inhibit the absorption of the composition absent its perforation by beam 5.1. Beam 6.1 can increase the temperature of the deeper layers of the skin thereby enhancing the efficacy of the composition on the deeper layers of the skin.

In a further non-limiting embodiment, the method provides a method of treating rhytides, scars, or wrinkles in the skin. The method can be practiced by contacting the skin with a first laser beam having a wavelength of about 980 nm, a second laser beam having a wavelength of about 1440 nm, and a third laser beam having a wavelength of about 1930 nm. The first beam having a wavelength about 980 nm produces deep penetration of the skin. The second beam having wavelength of about 1440 propagates into the subcutaneous collagen. The third beam having a wavelength of about 1930 nm ruptures the stratum corneum. The beams can contact the skin in a pattern of overlapping beams, partially overlapping beams, non-overlapping beams, or combinations thereof. The beams can contact the skin in pulse mode, continuous mode, or a combination thereof. Contacting the skin with the beams can be performed simultaneously with, or before, the administration of a composition comprising Botox™, fibroblasts, stem cell factors, one or more skin fillers, or combinations thereof. The composition can be administered from a reservoir within tip 3.

It will be understood that in embodiments wherein three or more laser beams are administered, laser system 1 will comprise additional laser sources and scanners in optical communication with one another as disclosed herein, such that the additional laser sources are adapted to produce the beam distribution patterns disclosed herein.

In a further non-limiting embodiment, the invention provides a method for treating telangiectasia and pigmented lesions. This method can be practiced by contacting the skin with a first laser beam having wavelength of about 532 nm, a second laser beam having a wavelength of about 540 nm, and third laser beam having a wavelength of about 980 nm. The skin can be contacted with the beams in a pattern selected from overlapping beams, partially overlapping beams, non-overlapping beams, and combinations thereof. The beam having a wavelength of about 980 nm provides preheating of the skin and deep propagation of the beam within the skin, while the beams having wavelengths of about 532 nm and about 540 nm destroy the small blood vessels of the skin and have a shallow propagation within the skin. This embodiment of the method can comprise topically administering an antiangiogenic agent (e.g. Avastin™ or Lucentis™) simultaneously or after contacting the skin with the beams to inhibit the re-appearance of the destroyed blood vessels. The antiangiogenic agent can be administered from a reservoir within tip 3.

In a further non-limiting embodiment, the invention provides a method for treating pigmented lesions wherein a first laser beam having a wavelength of about 532 nm, a second laser beam having a wavelength of about 980 nm, and a third laser beam having a wavelength of about 1550 nm contact a skin having pigmented lesions.

In some embodiments, the system and method of the invention is used to treat tissues selected from corneal tissue, gastrointestinal epithelium, endothelial tissue, urothelium tissue, parenchymal tissue, respiratory tissue, connective tissue, cartilage, fat, and retinal tissue. It is further contemplated that the system and method of the invention can be used to treat kidney stones and gall stones, wherein one or more beams of laser energy are contacted with the kidney stones or gall stones.

While illustrative embodiments of the invention have been described herein, the present invention is not limited to the various preferred embodiments described herein, but includes any and all embodiments having equivalent elements, modifications, omissions, combinations (e.g. of aspects across various embodiments), adaptations and/or alterations as would be appreciated by those in the art based on the present disclosure. The limitations in the claims are to be interpreted broadly based on the language employed in the claims and not limited to the examples described in the present specification or during prosecution of the application, which examples are to be construed as non-exclusive.

The invention claimed is:

1. A laser system for administering two or more beams of laser energy for tissue therapy, comprising:
    a) a first laser in optical communication with a first laser scanner that is adapted to distribute a beam from said first laser in a first pattern; and
    b) a second laser in optical communication with a second laser scanner that is adapted to distribute a beam from said second laser in a second pattern;
    c) wherein said first pattern and said second pattern combine to produce overlapping beams and non-overlapping beams.

2. The system of claim 1, wherein said lasers are adapted to produce beams having the same wavelength.

3. The system of claim 1, wherein said lasers are adapted to produce beams having different wavelengths.

4. The system of claim 2 or 3, wherein said same or different wavelengths are selected from about 540 nm, about 700 nm, about 810 nm, about 980 nm, about 1064 nm, about 1440 nm, about 1300 nm, about 1550 nm, about 1927 nm, about 1940 nm, about 2790 nm, and about 2940.

5. The system of claim 3, wherein said beams are a pair of wavelengths selected from about 1550 nm and about 1930 nm, about 980 nm and about 1550 nm, about 810 nm and about 1030 nm, about 1550 nm and about 1930 nm, about 532 nm and about 540 nm, about 532 nm and about 980 nm, about 1927 nm and about 1440 nm, and about 577 nm and about 980 nm.

6. The system of claim 1, wherein said lasers are solid-state lasers, laser diode lasers, gas lasers, chemical lasers, dye lasers, metal-vapor lasers, semiconductor lasers, or combinations thereof.

7. The system of claim 1, wherein said lasers are adapted to emit said beams in the same mode or a different mode.

8. The system of claim 7, wherein said mode is selected from pulse beam mode and continuous beam mode.

9. The system of claim 1, wherein said system comprises a tip.

10. The system of claim 9, wherein said tip is adapted to emit ultrasound energy, microwave energy, intensive pulse light energy, or combinations thereof.

11. A method of treating a tissue condition, comprising:
   a) contacting a tissue having a tissue condition with a first laser beam and a second laser beam, wherein said first laser beam and said second laser beam contact said tissue in a pattern that includes overlapping beams and non-overlapping beams;
   b) wherein contacting said tissue with said beams treats said tissue condition.

12. The method of claim 11, wherein said beams have the same wavelength.

13. The method of claim 11, wherein said beams have different wavelengths.

14. The method of claim 12 or 13, wherein said same or different wavelengths are selected from about 540 nm, about 700 nm, about 810 nm, about 980 nm, about 1064 nm, about 1440 nm, about 1300 nm, about 1550 nm, about 1927 nm, about 1940 nm, about 2790 nm, and about 2940 nm.

15. The method of claim 13, wherein said beams are a pair of wavelengths selected from about 1550 nm and about 1930 nm, about 980 nm and about 1550 nm, about 810 nm and about 1030 nm, about 1550 nm and about 1930 nm, about 532 nm and about 540 nm, about 532 nm and about 980 nm, about 1927 nm and about 1440 nm, and about 577 nm and about 980 nm.

16. The method of claim 11, wherein said beams are produced by solid-state lasers, laser diode lasers, gas lasers, chemical lasers, dye lasers, metal-vapor lasers, semiconductor lasers, or combinations thereof.

17. The method of claim 11, wherein said beams have the same mode or different modes.

18. The method of claim 17, wherein said mode is selected from pulse beam mode and continuous beam mode.

19. The method of claim 11, further comprising treating said tissue with ultrasound energy, microwave energy, intensive pulse light energy, or combinations thereof.

20. The method of claim 11, wherein said first beam and said second beam propagate in said tissue at different depths.

21. The method of claim 11, wherein said first beam and said second beam propagate in the same or different regions of said tissue.

22. The method of claim 21, wherein said beams damage said tissue in said regions.

23. The method of claim 11, wherein contacting said tissue with said beams causes said tissue to release one or more cytokines.

24. The method of claim 11, wherein said tissue is skin.

25. The method of claim 24, wherein said first beam propagates in the stratum corneum or epidermis, and said second beam propagates in the papillary dermis or all dermal layers of said skin.

26. The method of claim 24 or 25, wherein contacting said tissue with said beams treats a skin condition selected from wrinkles, loss of elasticity, skin photoaging, scars, rhytides, acne, telangiectasia, vitiligo, skin lesions, tattoo removal, blepharoptosis, and combinations thereof.

27. The method of claim 24, further comprising administering to said tissue a composition that comprises a drug, anti-angiogenic antibody, hyaluronic acid, botox, fibroblasts, stem cells, stem cell factors, a vitamin, an antioxidant, or combinations thereof.

28. The method of claim 11, wherein said tissue is selected from corneal tissue, gastrointestinal epithelium, endothelial tissue, urothelium tissue, parenchymal tissue, kidney stone, gallbladder stone, respiratory system tissue, connective tissue, cartilage, fat, retinal tissue, and combinations thereof.

* * * * *